US012225852B2

(12) United States Patent
Maor et al.

(10) Patent No.: US 12,225,852 B2
(45) Date of Patent: Feb. 18, 2025

(54) SYSTEM AND METHOD FOR PROTECTING HARVESTED FRUITS DURING HARVESTING

(71) Applicant: TEVEL AEROBOTICS TECHNOLOGIES LTD., Modiin (IL)

(72) Inventors: Yaniv Maor, Modiin (IL); Amit Shefi, Aseret (IL); David Swissa, Jerusalem (IL); Elad Shifman, Gedera (IL); Yuval Rothenberg, Beer Sheva (IL); Ran Cohen, Rishon Lezion (IL)

(73) Assignee: TEVEL AEROBOTICS TECHNOLOGIES LTD., Modiin (IL)

( * ) Notice: Subject to any disclaimer, the term of this patent is extended or adjusted under 35 U.S.C. 154(b) by 752 days.

(21) Appl. No.: 17/423,195

(22) PCT Filed: Jan. 15, 2020

(86) PCT No.: PCT/IL2020/050061
§ 371 (c)(1),
(2) Date: Jul. 15, 2021

(87) PCT Pub. No.: WO2020/148759
PCT Pub. Date: Jul. 23, 2020

(65) Prior Publication Data
US 2022/0061217 A1 Mar. 3, 2022

Related U.S. Application Data

(60) Provisional application No. 62/793,480, filed on Jan. 17, 2019.

(51) Int. Cl.
*A01D 46/20* (2006.01)
*A01D 46/22* (2006.01)
(Continued)

(52) U.S. Cl.
CPC ............ *A01D 46/20* (2013.01); *A01D 46/22* (2013.01); *A01D 46/253* (2013.01); *A01D 46/30* (2013.01);
(Continued)

(58) Field of Classification Search
CPC ...... A01D 46/20; A01D 46/22; A01D 46/253; A01D 46/30
See application file for complete search history.

(56) References Cited

U.S. PATENT DOCUMENTS 2,215,094 A * 9/1940 De Mars ............... B65B 25/046
53/239
2,670,921 A * 3/1954 Dodd ................... B65G 69/165
177/56
(Continued)

FOREIGN PATENT DOCUMENTS

CN 108633464 A 10/2018
DE 2256828 5/1973
(Continued)

OTHER PUBLICATIONS

Search Report for PCT/IL2020/050061 Completed Apr. 7, 2020 ; Mailed Apr. 29, 2020 2 pages.
(Continued)

*Primary Examiner* — Lucas E. A. Palmer
(74) *Attorney, Agent, or Firm* — The Roy Gross Law Firm, LLC; Roy Gross

(57) ABSTRACT

The present invention provides a fruit's protection system designed to be mounted onto a standard collection bin for safely placing harvested fruits inside the collection bin without harming same.

16 Claims, 16 Drawing Sheets

(51) Int. Cl.
*A01D 46/253* (2006.01)
*A01D 46/30* (2006.01)
*A01F 25/14* (2006.01)
*G01N 33/02* (2006.01)
*B64U 101/40* (2023.01)

(52) U.S. Cl.
CPC ........... *A01F 25/14* (2013.01); *G01N 33/025* (2013.01); *B64U 2101/40* (2023.01)

(56) References Cited

U.S. PATENT DOCUMENTS

| | | | | |
|---|---|---|---|---|
| 2,797,540 | A * | 7/1957 | Carlsen | B65B 25/046 53/244 |
| 2,910,193 | A * | 10/1959 | Lindeman | B65B 25/04 414/924 |
| 2,911,775 | A * | 11/1959 | Schwebs | B65D 75/28 53/145 |
| 3,348,714 | A * | 10/1967 | Ash | B60P 1/16 414/528 |
| 3,408,108 | A * | 10/1968 | Duda, Jr. | B62D 33/042 298/23 D |
| 3,928,942 | A * | 12/1975 | Paddock | B65B 35/38 53/247 |
| 3,948,401 | A * | 4/1976 | Spencer | B65D 19/14 222/386 |
| 4,233,802 | A * | 11/1980 | Booth | B65B 25/046 53/448 |
| 4,506,492 | A * | 3/1985 | Boyd | B65B 25/046 53/506 |
| 4,570,419 | A * | 2/1986 | Tinsley | B65B 25/04 53/247 |
| 4,660,352 | A * | 4/1987 | Deines | B65B 5/061 53/529 |
| 4,965,982 | A * | 10/1990 | Jesperson | B65B 25/046 53/248 |
| 5,007,227 | A * | 4/1991 | McClusky | B65B 25/046 53/392 |
| 5,072,100 | A * | 12/1991 | McClusky | B65B 25/046 235/98 R |
| 5,123,231 | A * | 6/1992 | Fallas | B65G 47/31 53/538 |
| 5,159,796 | A * | 11/1992 | Tas | B65B 25/046 53/248 |
| 5,325,653 | A * | 7/1994 | Boyd | B65B 25/046 141/192 |
| 5,502,949 | A * | 4/1996 | Main | B65B 25/046 53/448 |
| 5,661,949 | A * | 9/1997 | Blanc | B65B 25/046 53/154 |
| 5,794,415 | A * | 8/1998 | Huff | B65B 25/046 53/448 |
| 6,360,787 | B1 * | 3/2002 | Williamson | B65B 1/36 198/530 |
| 6,449,929 | B1 * | 9/2002 | Guardiola | B65B 25/04 53/567 |
| 8,033,084 | B1 * | 10/2011 | Peterson | B65B 5/10 53/473 |
| 10,005,572 | B1 * | 6/2018 | Minardi | B65B 5/06 |
| 2003/0000968 | A1 * | 1/2003 | Van Wijngaarden | B65B 25/046 222/196 |
| 2005/0028495 | A1 * | 2/2005 | Blanc | B65B 5/105 53/247 |
| 2005/0034961 | A1 * | 2/2005 | Aquarius | B65B 5/108 198/418 |
| 2006/0288880 | A1 * | 12/2006 | Hanks | B65B 25/046 99/485 |
| 2007/0209327 | A1 * | 9/2007 | Kent | B65B 25/046 53/553 |
| 2008/0223000 | A1 * | 9/2008 | Macdonald | B65B 25/046 53/244 |
| 2009/0134156 | A1 | 5/2009 | Hadar | |
| 2013/0118130 | A1 * | 5/2013 | Visser | A01K 43/00 53/235 |
| 2013/0174514 | A1 * | 7/2013 | Wilkinson | B65B 43/59 53/260 |
| 2020/0299072 | A1 * | 9/2020 | Blanc | B65B 25/045 |
| 2022/0177171 | A1 * | 6/2022 | Doughty | B65B 35/42 |

FOREIGN PATENT DOCUMENTS

| | | |
|---|---|---|
| WO | 2006038065 | 4/2006 |
| WO | 2018087546 A1 | 5/2018 |

OTHER PUBLICATIONS

Written Opinion of PCT/IL2020/050061 Completed Apr. 7, 2020 ; Mailed Apr. 29, 2020 8 pages.
European search report for EP20741344 dated Aug. 19, 2022.
International search report for PCT/IL2020/050061 dated Apr. 29, 2020.
Written opinion for PCT/IL2020/050061 dated Apr. 29, 2020.

* cited by examiner

SYSTEM AND METHOD FOR PROTECTING HARVESTED FRUITS DURING HARVESTING

CROSS REFERENCE TO RELATED APPLICATIONS

This application is a National Phase of PCT Patent Application No. PCT/IL2020/050061 having International filing date of Jan. 15, 2020, which claims the benefit of priority of U.S. Provisional Patent Application No. 62/793,480, filed Jan. 17, 2019, the contents of which are all incorporated herein by reference in their entirety.

FIELD OF THE INVENTION

The present invention is in the technical field of agriculture technology, specifically autonomous harvesting, more particularly, the present invention relates to harvesting—devices, systems and methods. More particularly, the present invention relates to harvesting devices for orchards, plantations green houses and field, such as apple-, pear-, apricot-, peach-, orange-, small-citrus fruit-, and lemon-trees, avocado, vines, tomatoes, eggplants, cucumbers, and peppers.

BACKGROUND

Conventional orchards harvesting is done by deployment of fruit collection bins between the tree lines, before manual workers arrive to pick the fruit and fill the bins. The bins are evenly spread throughout the orchard prior to harvesting. In most cases, the bin is placed on the ground and carried by a forklift. Alternatively, the bins are equipped with wheels or mounted on a cart and pulled by a tractor to their designated location. After deploying the bins on the ground, human- or robotic-pickers get in between the tree-lines, start harvesting and fill the bins with harvested fruits.

When a bin is filled with fruit, the pickers move to the next tree line, while a forklift or a dedicated track takes the full bin for storage, shipment or any other action. Today, bins are usually taken to a warehouse for storage/cooling, and are removed/shipped according to market demand.

Notably, only after taken out from storage, the bin is taken to a sorting house for sorting the fruits. Only after sorting of the fruit it is possible to evaluate the economic value of each bin and each fruit therein. As a result, there is no way of knowing the real value of each bin within a warehouse, let alone the number of fruits and their quality.

In all known robotic systems, the bins are mounted and installed on a harvester-robot or on a track to facilitate easy access of the harvesting arms to the bin for deployment of the fruits therein.

The disadvantage with human harvesting and known robotic systems is that the harvested fruits are thrown into the collection bin, which may lead to damaged fruits—either due to hitting the bottom of the bin or from hitting another fruit. This means that the fruits' value within a collection bin is dramatically reduced due to the presence of damaged fruits, which may further cause undamaged fruits to spoil.

There are some complicated and expensive bin-fillers that are used in warehouse or other robotic solutions made of a carousel that rotate inside the bin and move the fruit from the top side to the floor. These machines are complex, heavy, expensive and do not distribute the fruits uniformly on the ground, so human involvement is required to make sure the fruits are leveled (i.e. create a flat layered surface).

Accordingly, a need exists for a more efficient technique and system for collecting harvested fruits that saves harvesting time, reduces costs, and prevents fruits' damage.

SUMMARY

The present invention provides a fruit protection system for use with a fruit collection bin for protecting fruits from damage during harvesting, the system comprising: (a) a fruit movable elevator floor/floating floor designed to fit said fruit collection bin; and (b) at least one retraction mechanism for lifting said elevator floor/floating floor, wherein said elevator floor/floating floor can descend and ascend.

The present invention further provides a method for preventing/reducing damage to fruits during harvesting, the method comprising the steps of: (a) mounting/attaching a fruit protection system according to the invention onto a fruits' collection bin or onto a bin's wagon; (b) placing harvested fruits onto the elevator floor/floating floor of said fruit protection system; and (c) gradually lowering said elevator floor/floating floor to the bottom of the collection bin.

Notably, harvesting robots, such as flying robots and robotic arms, can place fruits on the elevator floor/floating floor dispersed uniformly, since they have full flexibility to place it one by one in different positions.

In certain embodiments, the elevator floor/floating floor has a small slope (e.g. 3 degrees) so the fruit will role to one side when desired.

In certain embodiments, of the fruits protection system of the invention, the elevator floor/floating floor is moved down autonomously by the weight of the fruits placed thereon or mechanically/electronically by a motor(s) similar to an elevator.

BRIEF DESCRIPTION OF THE DRAWINGS

FIGS. 7A-7C illustrate a configuration in which the rod-shaped floor segments move left and right to generate gaps; and FIGS. 7D-7EC illustrate a configuration in which the rod-shaped floor segments move up/down to generate gaps.

DETAILED DESCRIPTION

Today, during harvesting in an orchard, human or robotic harvesters pick fruits and discharge the harvested fruits in designated collection bins. When a bin is full, it is carried away with a forklift to a storage warehouse. However, the discharging of the fruits into the collection bin usually damages the fruits as they are dropped to the hard bottom of the collection bin from a height, e.g. from the edge of the bin's walls all the way down to the bottom.

Figure 1:
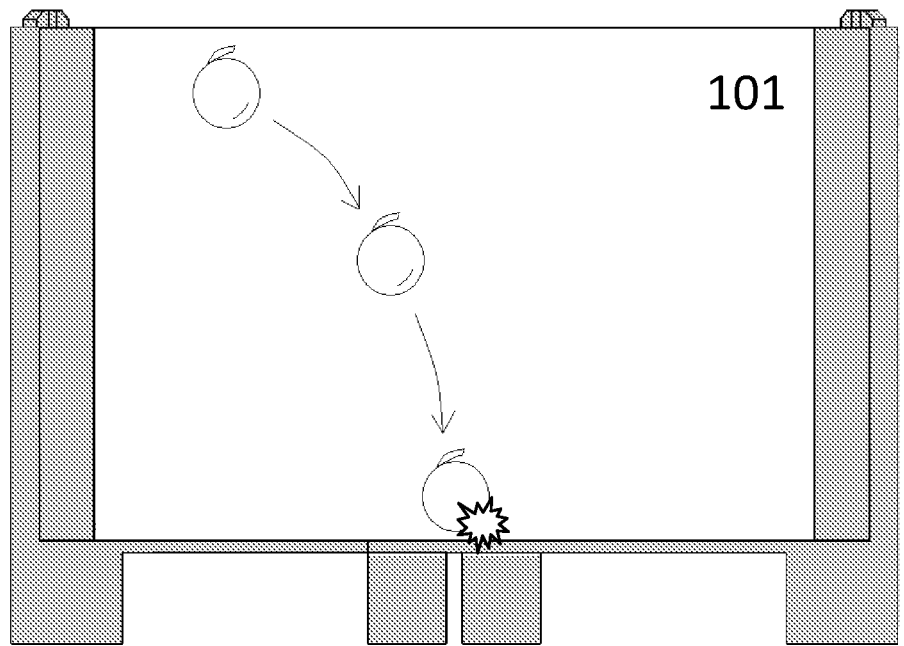
FIG. 1 is an illustration of how a fruit thrown into a standard collection bin may be damaged when hitting the floor of the collection bin.

As well known, a fruit thrown into a collection bin may be damaged when hitting the hard floor of the collection bin (illustrated in FIG. 1) or when hitting other fruits in the bin. Such damage shortens the shelf life of the fruits and reduces their value. As such, it is advisable to reduce to a minimum any damage caused to fruits during collection. Notably, the damage may occur not only to the actual falling fruit, but also to other fruits already residing in the collection bin that are hit by the fallen fruit(s).

As explained above, when harvesters (human or robotic) fill the collection bins, the fruits fall to the bottom of the bin and subsequently hit the bottom of the bin or the uppermost fruits in the bin. Such hitting may damage the fruits, which reduces the fruits' economic value. Moreover, damage during harvesting may cause decay during storage, resulting with rotten stored fruits, which may spread to non-damaged nearby fruits. Accordingly, it is advisable to reduce damage caused to fruits during the filling of a collection bin. Notably, every damaged fruit has a negative value (not just zero) since the storage cost is also wasted. The value of high-quality fruit is several times higher than standard quality fruit.

Accordingly, the present invention provides a fruit protection system for use with a fruit collection bin for protecting fruits from damage during harvesting, the system comprising: (a) a fruit movable elevator floor/floating floor 105 designed to fit the fruit collection bin 101; and (b) at least one retraction mechanism 106 for lifting the elevator floor/floating floor 105, wherein the elevator floor/floating floor 105 can descend and ascend.

It should be noted that the fruit protection system of the invention is an addition or add-on to existing collection bins or wagons, and that the terms "elevator", "elevator floor", "elevated bottom", "floating floor" and "bottom surface" as used herein interchangeably do not refer to the bottom of the actual collection bin but to a pseudo-bottom that can be lifted up and down in the collection bin regardless of the bin's bottom section. Moreover, the addition of a fruit protection system of the invention to a fruit collection bin does not affect the inner volume of the bin and does not reduce its capacity.

Accordingly, before picking starts, the elevator of the fruit protection system is located at its highest point, e.g. the height of the upper side of the bin, thereby enabling placement of the fruits thereon, i.e. on the top of the elevator floor 105, while eliminating the falling of the fruits all the way to the bottom of the collection bin 101. In certain embodiments, the elevator floor 105 is pushed down by the weight of the picked fruits and moves down slowly. The movement of the elevator floor 105 depends on the fruits' weight. This procedure prevents fruits' bruising and improves harvesting effectiveness since it also saves picking time—now the harvesting robots or human pickers do not need to slowly and gently open the fruit basket into the collection bin 101. It should be noted that even when the elevator floor 105 is located at its highest point, i.e. essentially leveled with the collection bin's walls, the top edge of the bin's walls is still a bit higher than the top surface of the elevator floor 105 in order to create a barrier that prevents rolling of the fruits off the elevator floor 105 to the ground outside the collection bin 101.

In certain embodiments, the fruit protection system of the invention is provided/installed in a box/frame that is designed to be mounted on the upper edges of the collection bin's side walls. FIG. 2C illustrates how a standard collection bin 101 looks like when equipped with a box holding a fruit protection system of the invention with an elevator floor 105. It should be noted that the box/frame can be mounted on the external side wall of the collection bin 101 or on the wagon; inside the collection bin 101 (i.e. between the bin's walls); or on top of the bin, i.e. placed on the upper edge of the bin's walls. It should be noted that the box/frame of the system, when present, serves also a fruits' barrier that prevents rolling of the fruits off the elevator floor 105 to the ground outside the collection bin 101.

In certain embodiments of the fruit protection system of the invention, the location/position/height of the elevator floor 105 is determined according to the weight of the fruits placed thereon and the retraction force of the at least one retraction mechanism 106.

In specific embodiments of the fruit protection system of any of the embodiments above, when the fruit collection bin 101 is empty, the elevator floor 105 is positioned in its upmost upper position, ready to receive fruits and descend according to need/fruits' weight. In further specific embodiments, when the fruit collection bin 101 is completely full, the elevator floor 105 is positioned in its lowest position at the bottom of the collection bin 101 covered with fruits. In alternative specific embodiments, when the fruit collection bin 101 is completely full, the elevator floor 105 is positioned in its upmost upper position, without any fruits placed thereon—this can be obtained by, e.g. pulling the elevator floor 105 from the bottom of the collection bin 101 after it is filled, or the elevator floor 105 may be made of disposable material that degrades thereby leaving the collection bin 101 with the fruits and without the elevator floor 105.

It should be noted that the elevator floor 105 and retention mechanism can be made of any suitable material. For instance, both can be made from the same material and constitute the same unit, e.g. as an elastic sheet of material that is assembled onto the collection bin 101 by attaching the edges of the sheet to the bin's walls, such that the elasticity of the sheet serves as the retention mechanism (see illustrated in FIGS. 4C & 4D). Accordingly, in certain embodiments of the fruit protection system of any of the embodiments above, the elevator floor 105 is made of a flexible and/or disposable material. In alternative specific embodiments, the elevator floor 105 is a stretchable leash/sheet that starches according to the fruits' weight placed thereon. In further alternative specific embodiments, the elevator floor 105 is a stretchable mesh that starches according to the fruits' weight placed thereon.

Alternatively, in certain embodiments of the fruit protection system of any of the embodiments above, the elevator floor 105 and the retention mechanism are made from different substances. For instance, the retention mechanism may be made of metal, such as metal springs, or made of elastic material such as rubber or silicon, and the elevator door is made of wood, plastic, metal, etc. or any combination thereof.

In specific embodiments of the fruit protection system of any of the embodiments above, the elevator floor 105 is designed to descend when a certain amount or weight of fruits is accumulated thereon, release the fruits at the collection bin's bottom, and ascend to its original upper position for receiving more fruits. In such configuration, when the fruit collection bin 101 is completely full, the elevator floor 105 is positioned in its upmost upper position, without any fruits placed thereon. Such a configuration can be obtained by, e.g. creating passageways/opening within the elevator floor 105 through which fruits can pass as when the elevator floor 105 is at the lowest position within the collection bin 101, which enables lifting the fruitless elevator floor 105 back up to its original upper position.

Accordingly, in certain embodiments of the protection system of any of the embodiments above, the elevator floor 105 is made of or constitutes movable/shiftable fragments having a closed-orientation in which fruits cannot pass between the fragments, thereby serving as a platform for placing fruits thereon; and an open-orientation in which fruits can pass between the fragments when needed, thereby releasing an fruits placed thereon on the bottom of the collection bin 101 or on top of fruits within the collection bin 101 gently without causing damage thereto.

Accordingly, in specific embodiments of the fruit protection system with an elevator floor 105 that is made of or constitutes movable/shiftable fragments, the movable/shiftable fragments: (i) move toward one another along a plane parallel to the bottom of the collection bin 101 (into an essentially overlapping position); (ii) rotate on an axis that extends in the lengthwise direction of the fragments; or (iii) move up and/or down relative to one another in a diagonal angle to the bottom of the collection bin 101.

The mechanism that is responsible for the lifting up and down of the elevator floor 105 is the retraction mechanism 106. Any suitable mechanism can be used, and can be either autonomous based on gravity and elasticity of the material from which it is made, such as rubber bands or metal springs, or may be controlled, e.g. by electric motor controlled by a computing system.

Accordingly, in certain embodiments of the fruit protection system of any of the embodiments above, the at least one retraction mechanism 106 is: (i) a spring located below the elevator floor 105; (ii) an elastic strap(s) or spring(s) designed to be attached to the walls of the collection bin 101; (iii) an electric motor(s) based mechanism; or (iv) a pneumatic mechanism, or any combination thereof.

In further specific embodiments, the fruit protection system of any of the embodiments above further comprises a computing system comprising a memory and processor. Such computing system may be designed to receive data regarding the amount and/or weight of the fruits placed on the elevator floor 105 and/or inside the collection bin 101.

In certain embodiments, the computing system of the fruit protection system of the invention further comprises an algorithm for determining a fruit's quality inside each collection bin 101. In certain embodiments, said algorithm for determining the fruit's quality uses at least one of the following parameters for determining the fruit's quality, including ripeness, according to the type of fruit being harvested: color, water content, rigidity/softness, sparkle, size, season, spots-damages inspection, fruit disconnection force (the ripper the fruit is—the easier it is to pull), weight.

In certain embodiments, the computing system of the fruit protection system of the invention enables the elevator floor 105 to be completely independent/autonomous so that there is no need for a manual control thereof.

The above described fruit protection system is designed to minimize the impact forces on fruits that are deposited in a collection bin 101, thereby reducing the risk of damaging thereof and subsequently increasing their shelf life and overall value.

In certain embodiments, the present invention further provides a method for preventing/reducing damage to fruits during harvesting, the method comprising the steps of: (a) mounting/attaching a fruit protection system according to any of the embodiments above onto a fruits' collection bin 101; (b) placing harvested fruits onto the elevator floor 105 of the fruit protection system; and (c) gradually lowering the elevator floor 105 to the bottom of the collection bin 101.

In certain embodiments of the above method for preventing/reducing damage to fruits, the mounting/attaching of the fruit protection system onto a fruits' collection bin 101 is performed manually or automatically by robotic machinery. It should be noted that the fruit protection system can be mounted: (i) on the external side wall of the collection bin 101; (ii) inside the collection bin 101 (i.e. between the bin's walls); or (iii) on top of the bin, i.e. placed on the upper edge of the bin's walls or on the wagon. The assembling is designed to be simple to enable fast dismantling and optionally reassembly on another collection bin 101, even in the orchard.

In certain embodiments of the above method for preventing/reducing damage to fruits, step (b) of placing harvested fruits onto the elevator floor 105 is carried out by human workers or by robotic harvesters. The placement of the fruits on the elevator floor 105 may be one at a time (e.g. when using a harvesting UAV or a robotic arm that pick and deliver a single fruit at a time) or in bulk (e.g. emptying a collection bag/basket by a human picker or emptying a harvesting UAV carrying more than one fruit).

In specific embodiments, a harvesting UAV places each fruit at a different place on the elevator floor, while software management distributes the fruits uniformly on the elevator floor.

In certain embodiments of the above method for preventing/reducing damage to fruits, the position of the elevator floor 105 is such that the upper surface of the elevator floor 105 or the fruits placed thereon is essentially parallel to the upper edge of the collection bin's walls, such that fruits placed thereon do not fall to the bottom of the bin. It should be noted that the elevator floor 105 is leveled such that the collection bin's walls (or walls of a frame/box of the system) prevent rolling of the fruits off the elevator floor 105 to the ground outside the collection bin 101.

In specific embodiments of the above method for preventing/reducing damage to fruits, the lowering of the elevator floor 105 is in accordance with the fruits' weight. The lowering of the elevator floor 105 may be simply due to gravity and fruits' weight, or may be computer-controlled, i.e. using electrically-mechanic elements that are controlled by a computing system that determines when to lift the elevator floor 105 up and down, e.g. according to the number and/or weight of fruits placed on the elevator floor 105. In specific embodiments, the elevator floor 105 is lowered to the bottom of the collection bin 101 as fruits are piled thereon, and does not lift back up, but remains underneath the fruits at the bottom of the collection bin 101. In alternative specific embodiments, the elevator floor 105 is removed from the collection bin 101 after the bin is completely full. In further specific alternative embodiments, the elevator floor 105 is lifted down and up continuously during the filling of the collection bin 101, so that every time the elevator floor 105 is lifted down it delivers a few fruits to the bottom of the collection bin 101 or to the top layer of fruits therein, releases the fruits unharmed, and lifts back up to receive more fruits. This procedure is repeated until the collection bin 101 is filled.

Accordingly, in specific embodiments of the method for preventing/reducing damage to fruits, step (c) comprises: (i) maintaining the position of the elevator floor 105 at top position such that the upper surface thereof is parallel to the upper edge of the collection bin's walls while still creating a barrier (e.g. from the bin's walls) that prevents fruits from falling off the elevator floor 105 to the ground outside the collection bin 101; (ii) once a predefined weight/amount of fruit is placed on the elevator floor 105, lowering same to the bottom of the collection bin 101 or to the upper layer/surface of the fruits within the bin; (iii) releasing the fruits from the elevator floor 105 (so that they reside on the bin's bottom or on previously placed fruits); (iv) lifting the elevator floor 105 back to the top position and receiving/reloading new fruits; and (v) repeating the above steps (i)-(iv) until the collection bin 101 is filled.

The releasing of the fruits from the elevator floor 105 can be done in any suitable manner. In specific embodiments, the releasing of the fruits from the elevator floor 105 is carried out by opening gaps between fragments that constitute the elevator floor 105, e.g. by sliding fragments closer together, or by spacing gaps between the fragments, e.g. by moving upper fragments up or lower fragments down, or both. In alternative specific embodiments, the releasing of the fruits from the elevator floor 105 is carried out by twisting/turning fragments that constitutes the elevator floor 105 thereby creating gaps between adjacent fragments through which fruits can pass, e.g. twisting the fragments on a longitudinal axis. In further alternative specific embodiments, the releasing of the fruits from the elevator floor 105 is carried out by folding the fragments to create gaps.

In certain embodiments of the method for preventing/reducing damage to fruits, step (b) of placing the fruits on the elevator/floating floor is carried out by harvesting robot(s), such a flying harvesting robot or harvesting arm. In specific embodiments, the harvesting robot places the fruits on the floating floor in a uniform manner one by one, each fruit in a different position/location on the floating floor such that an even layer of fruits is formed on the floor (thereby avoiding creation of a pile of fruits).

In specific embodiments, the fruit protection system according to any of the embodiments above further comprises an integrated autonomous harvesting system that comprises, e.g. unmanned aircraft vehicles (UAV) or robotic harvesting arm(s). Such a collection bin 101 configuration reduces damage to harvested fruit, since they are placed directly on the elevator floor 105 or on top of previously harvested fruits located at the top area of the collection bin 101, and do not fall all the way to the bottom of the bin, which may damage them and/or other fruits already present in the collection bin 101.

Figure 2A:
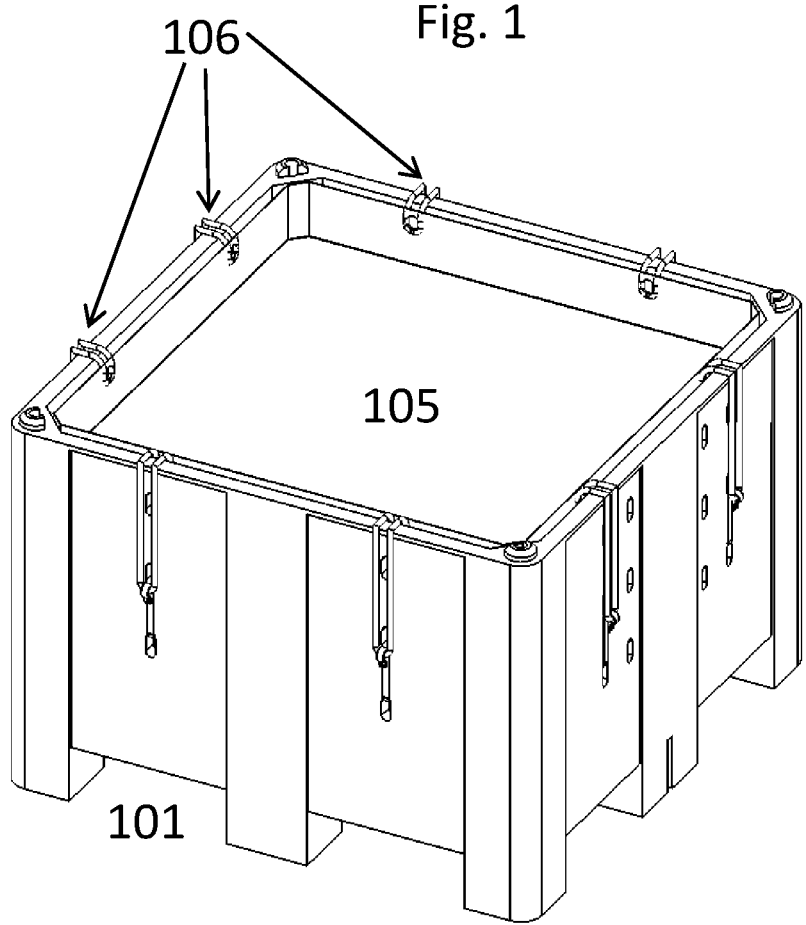
FIGS. 2A-2C are illustrations of a standard collection bin with an addition of a descending and ascending elevator floor/floating floor.
Figure 2B:
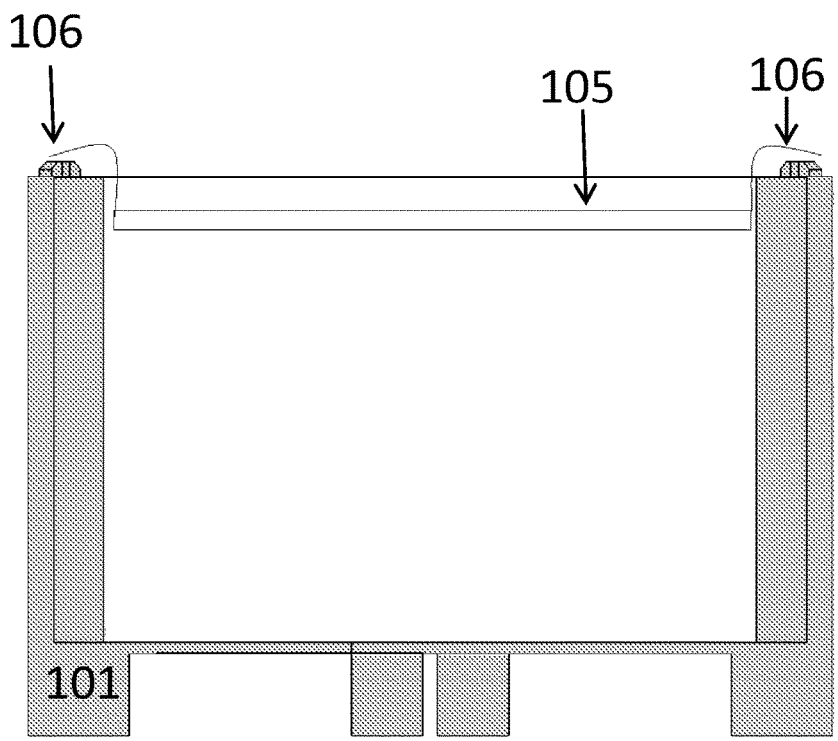
Figure 2C:
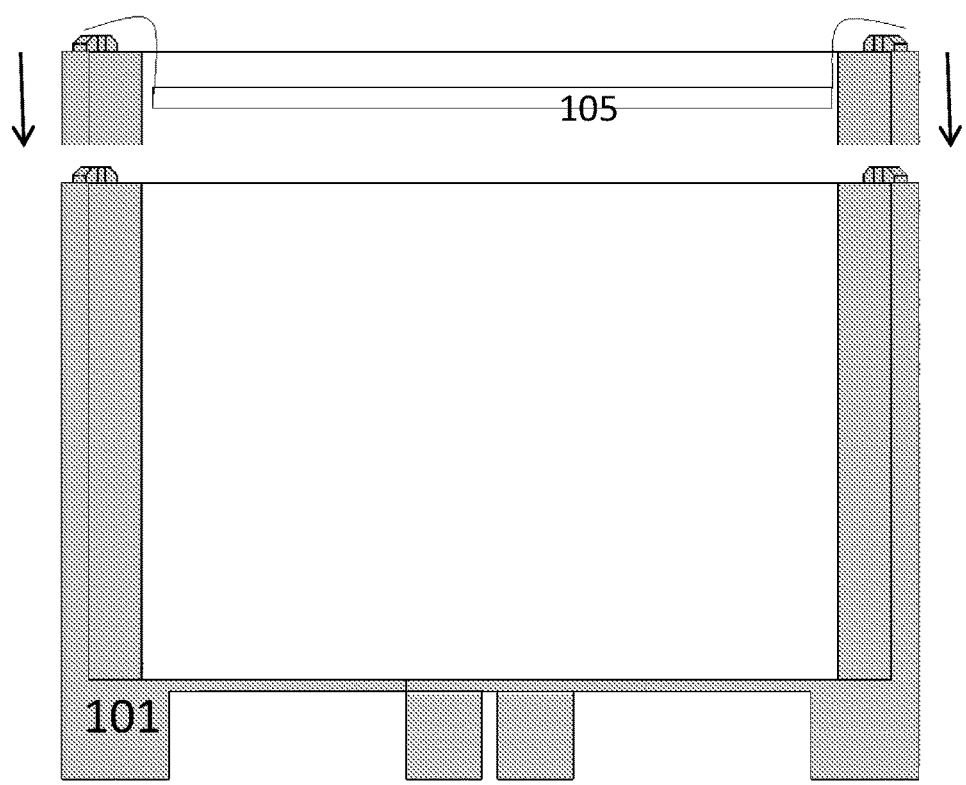

Reference is now made to FIGS. 2A-2C, which illustrate a standard collection bin 101 equipped with a fruit protection system of the invention with a descending and ascending bottom surface 105. The system is assembled directly onto the bin's walls (FIGS. 2A & 2B) or assembled by using a box/frame that is mounted onto the upper edge of the bin's walls (FIG. 2C). As seen in FIGS. 2A & 2B, the bottom surface 105 may be connected to the walls of the bin using suitable retraction springs 106, such as elastic bands, or the bottom surface 105 may be placed onto springs or spring-like mechanisms positioned on the bin's bottom (see e.g. in FIG. 4B). These retraction springs 106, enable the bottom surface 105 to descend as fruits are placed thereon (due to the increasing weight thereof), thereby maintaining the upper level of the fruits in the bin at the highest point (i.e. essentially leveled with the bin's walls' upper section) to reduce the distance the fruits have to fall.

Figure 3A:
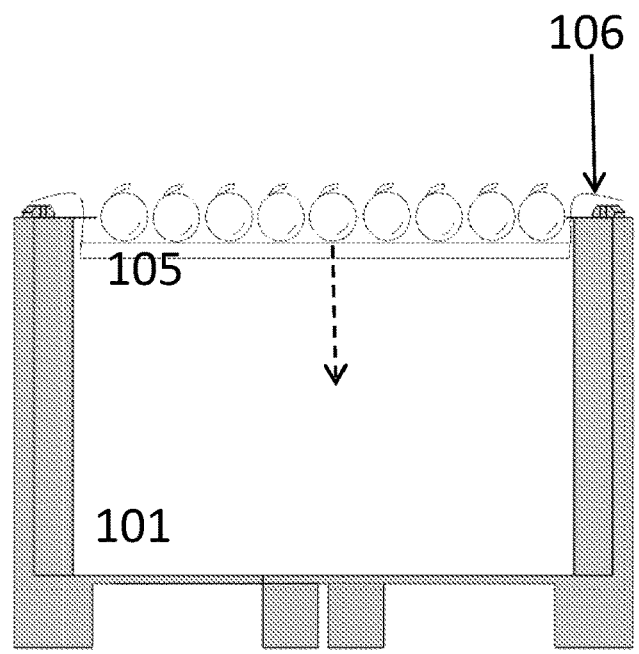
FIGS. 3A-3D illustrate how a descending and ascending elevator floor/floating floor according to the invention descends as fruits are piled thereon.
Figure 3B:
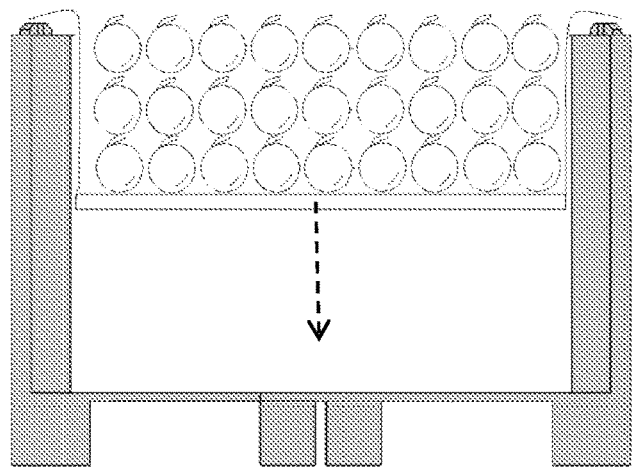
Figure 3C:
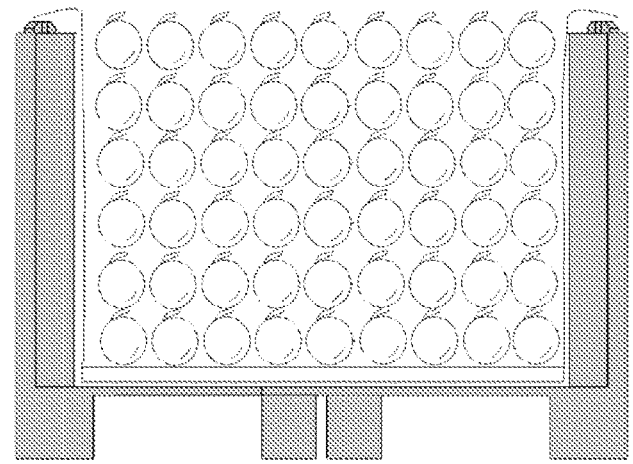
Figure 3D:
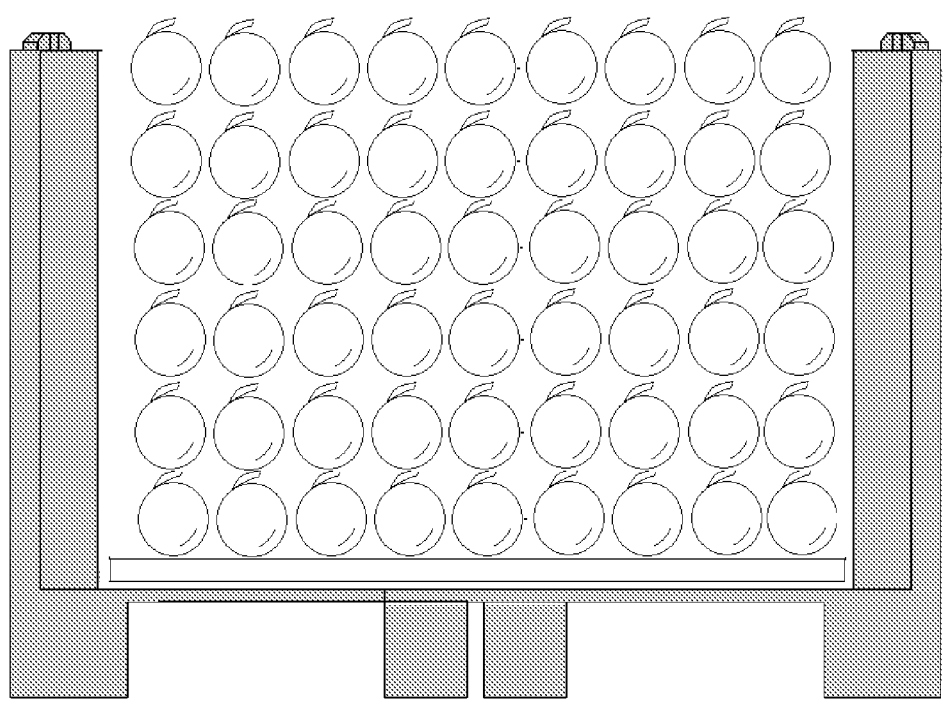

FIGS. 3A-3C illustrate how the bottom surface 105 descends as fruits are piled up. FIG. 3D illustrates that it is possible to remove the retraction springs 106 once the bin is full (e.g. for use in another bin). In specific embodiments, the bottom surface 105 is connected to the retraction springs 106 and both can be removed once the bin is filled (e.g. when the bottom surface 105 is made of flexible material—see e.g. FIGS. 4C & 4D), and transferred to another collection bin 101.

Figure 4A:
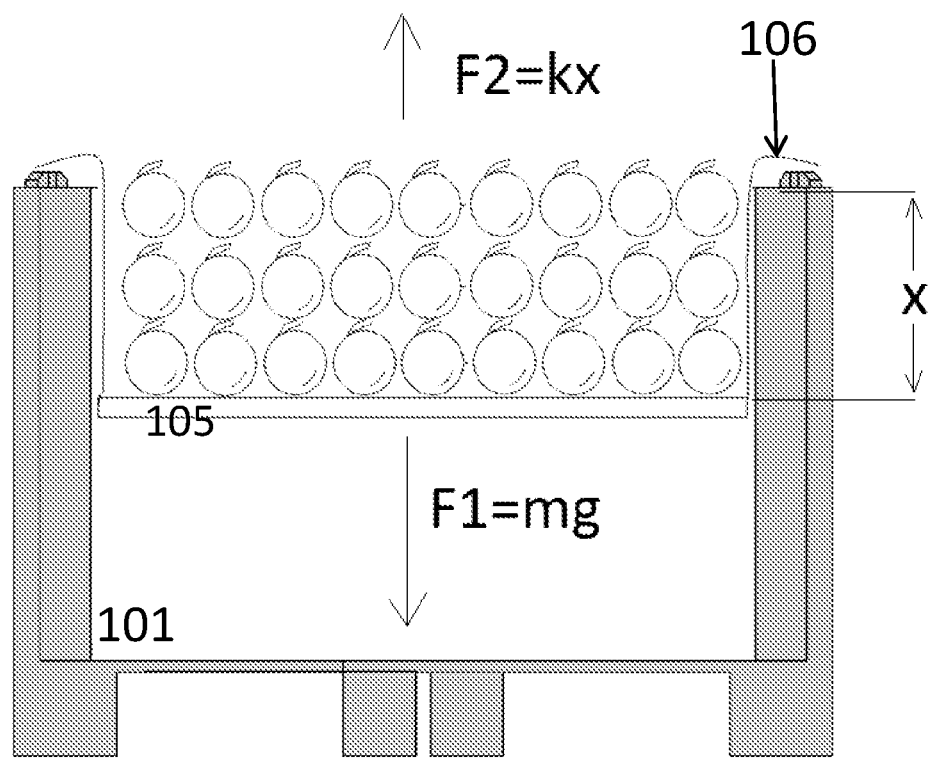
FIGS. 4A-4D illustrate the balance between the descending and ascending of the elevator floor/floating floor according to fruits' weight and retraction spring's force.
Figure 4B:
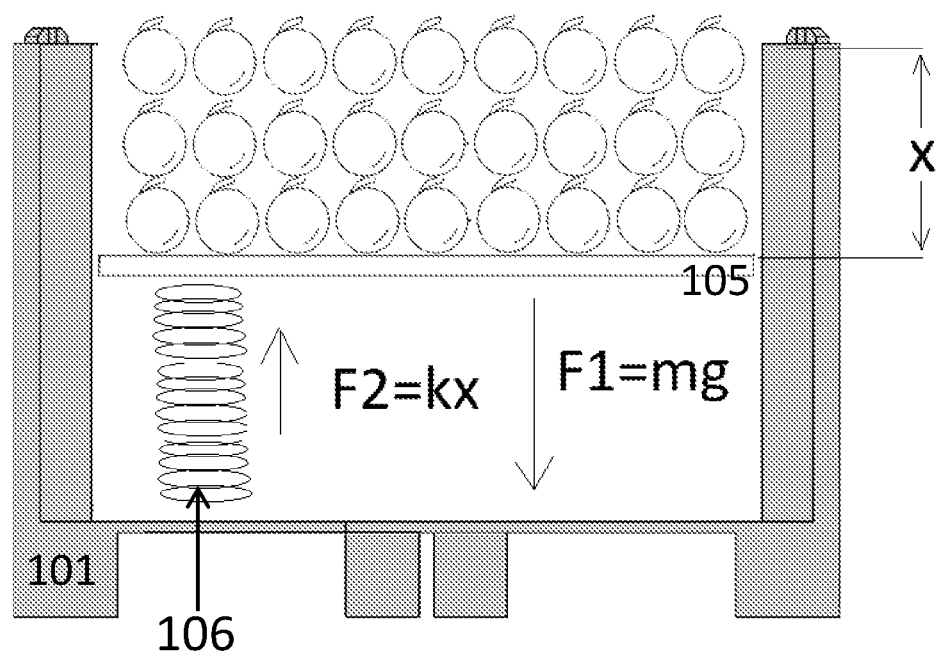
Figure 4C:
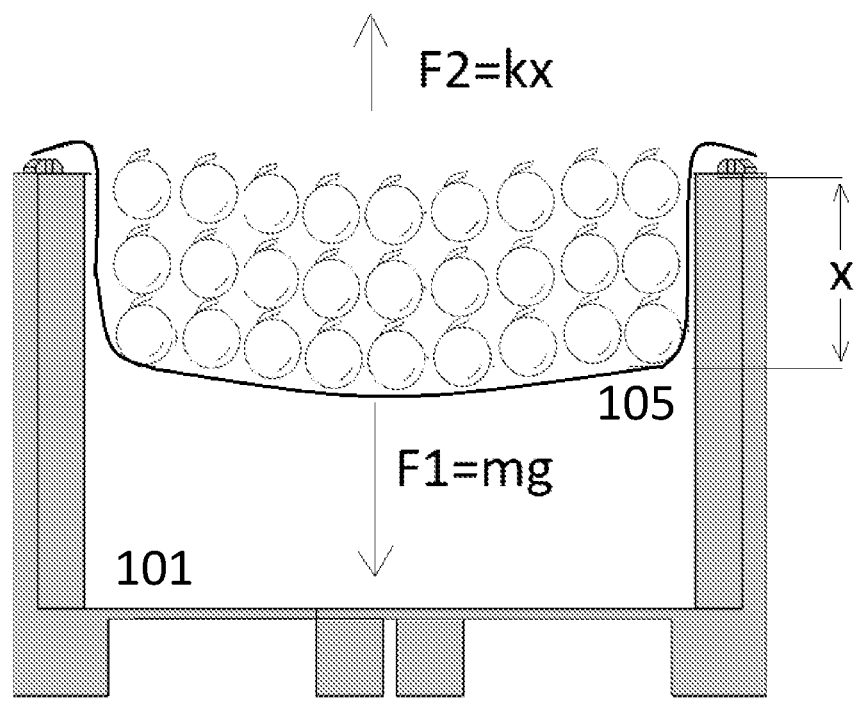
Figure 4D:
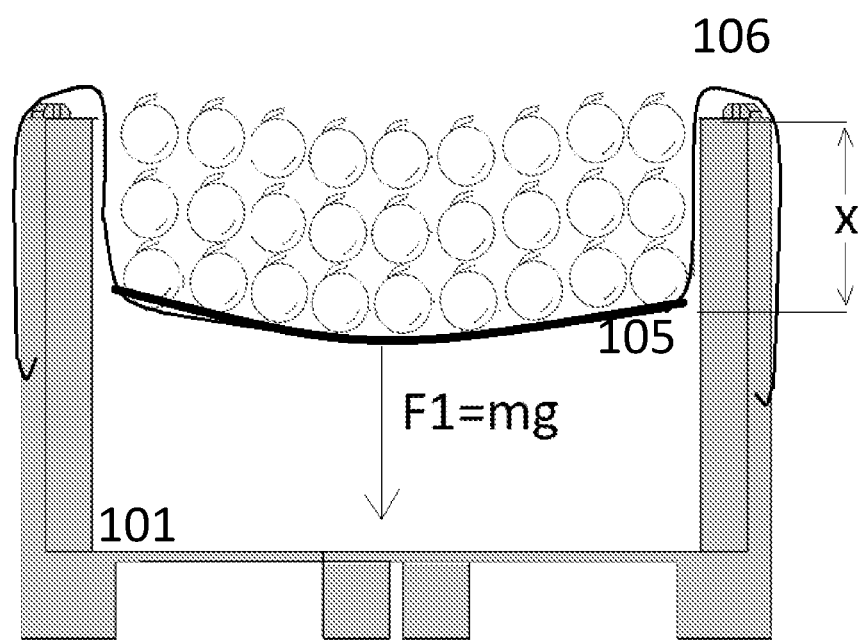

The balance between the descending and ascending of the bottom surface 105 according to fruits' weight and retraction spring's force is illustrated in FIG. 4A-4D: FIG. 4A shows that the gravity force of fruit is balanced with the leash/spring force which depends on the spring constant k and the length of the leash/retraction spring 106; and FIG. 4B shows that the pull-up force pulling the fruits upward can be obtained by leash/retraction spring 106 from the top of the bin and/or one or more springs positioned at the bottom of the bin. FIGS. 4C and 4D also illustrate the balance between gravity force with the elevator floor's force when the elevator floor 105 is made of a flexible/retraced material and optionally when the retraction mechanism 106 and the elevator floor 105 are made of the same elastic material.

Figure 5A:
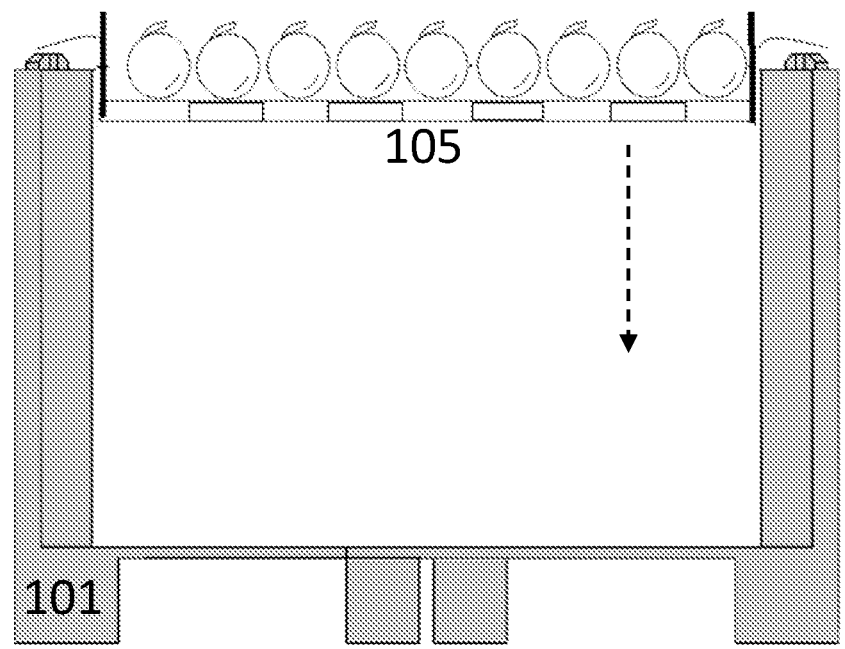
FIGS. 5A-5E illustrate one configuration of an elevator floor/floating floor according to the invention comprising retractable floor segments that enable fruits to pass therethrough when the elevator floor/floating floor reaches the bottom of the collection bin.
Figure 5B:
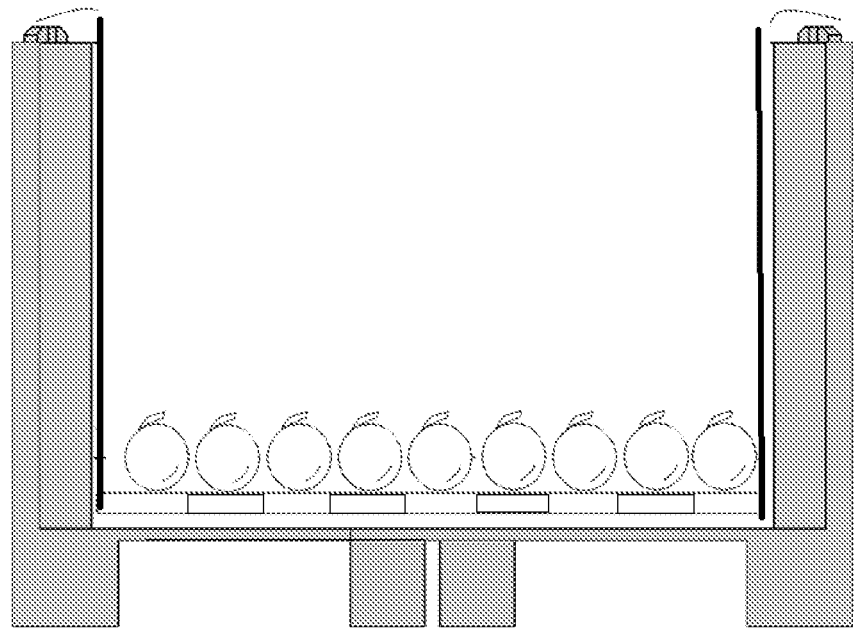
Figure 5C:
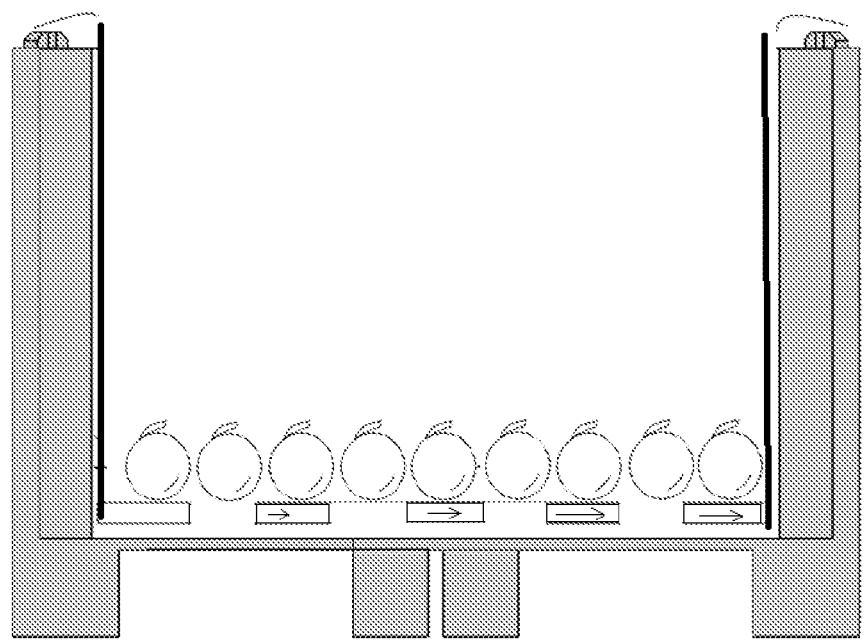
Figure 5D:
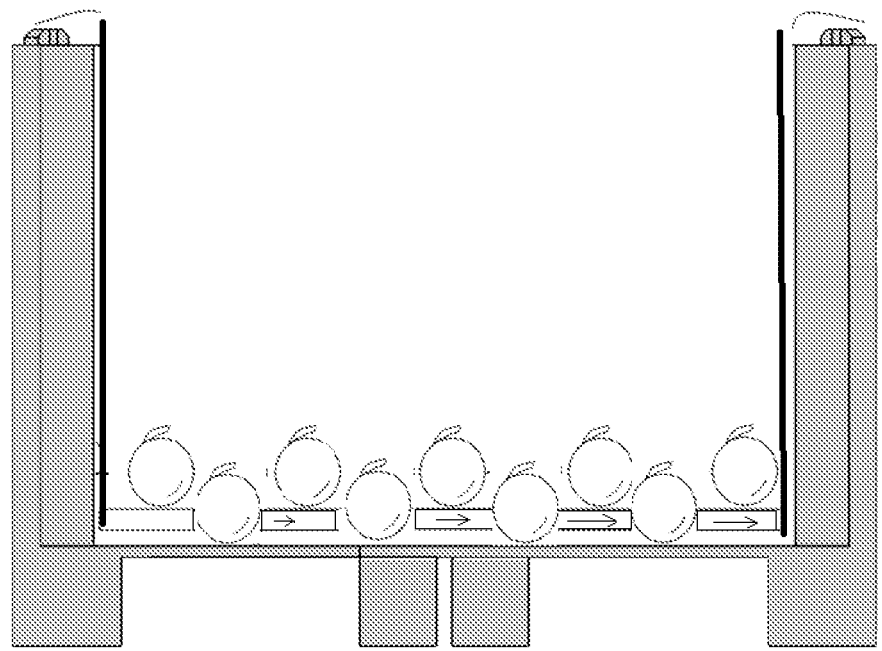
Figure 5E:
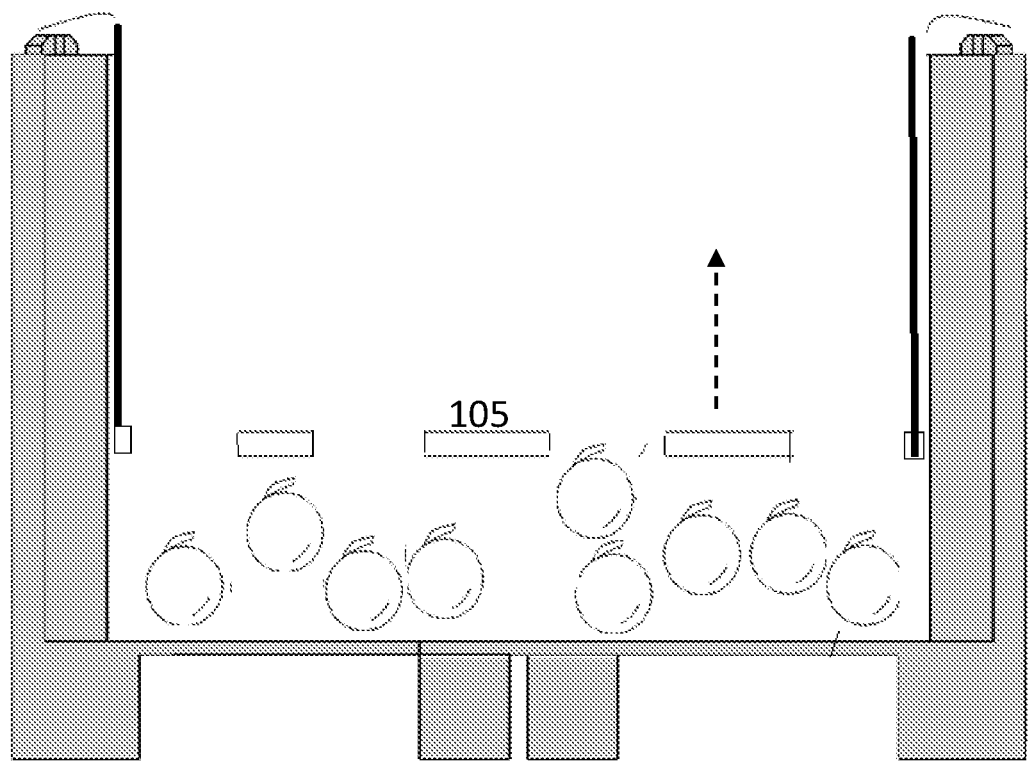

FIGS. 5A-5E illustrate the mechanism of action of a fruit protection system that comprises an elevator floor 105 made of movable/shiftable fragments that can slide towards one another to generate gaps in between for allowing fruits to pass. As illustrated, at the beginning the elevator floor 105 is position at an upper position enabling safe placement of fruits thereon without the fruits rolling off the floor to the ground and without throwing the fruits into the bottom of the collection bin 101 (FIG. 5A). Once the elevator floor 105 is full, or reached a predefined weight, it is lowered to the bottom of the collection bin 101 (or to the upper level of fruits within the bin) (FIG. 5B)—this lowering is either according to gravity or electrically by motor(s) controlled by an integrated computing system. When the elevator floor 105 has reached the lowest possible position (either at the bin's bottom or the upper level of fruits within the bin), the movable/shiftable fragments move towards one another—either in an overlapping manner or into one another (FIG. 5C), or the fragments move up or down relative to one another, thereby generating gaps through which fruits can pass (FIG. 5D) as the elevator floor 105 is lifted up (FIG. 5E). When the elevator floor 105 returns to its upper position, the movable/shiftable fragments return to their place creating a sealed floor onto which fruits can be placed. This procedure continues until the collection bin 101 is full.

Figure 6A:
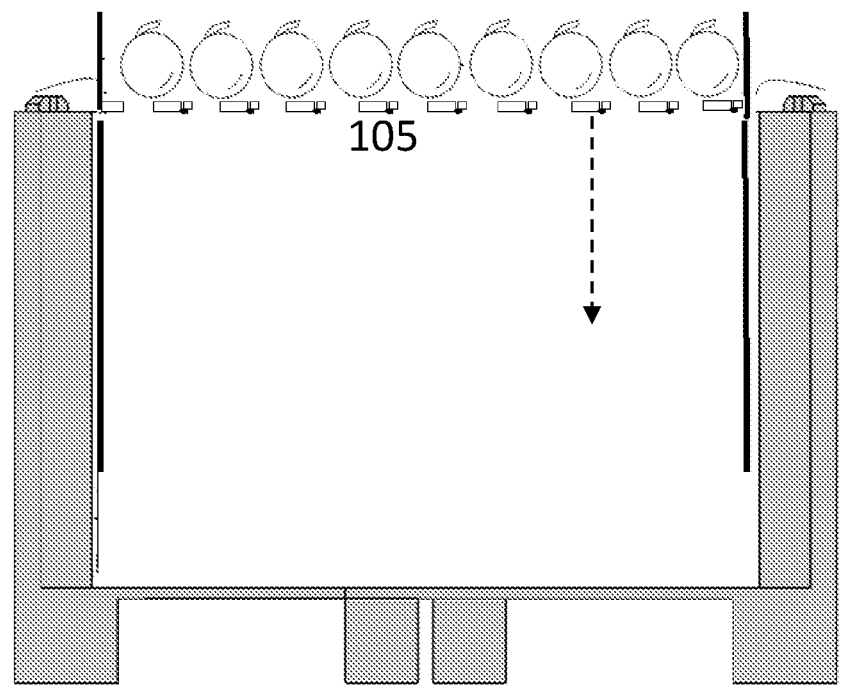
FIGS. 6A-6E illustrate another configuration of an elevator floor/floating floor according to the invention comprising folding floor segments that enable fruits to pass therethrough when the elevator floor/floating floor reaches the bottom of the collection bin.
Figure 6B:
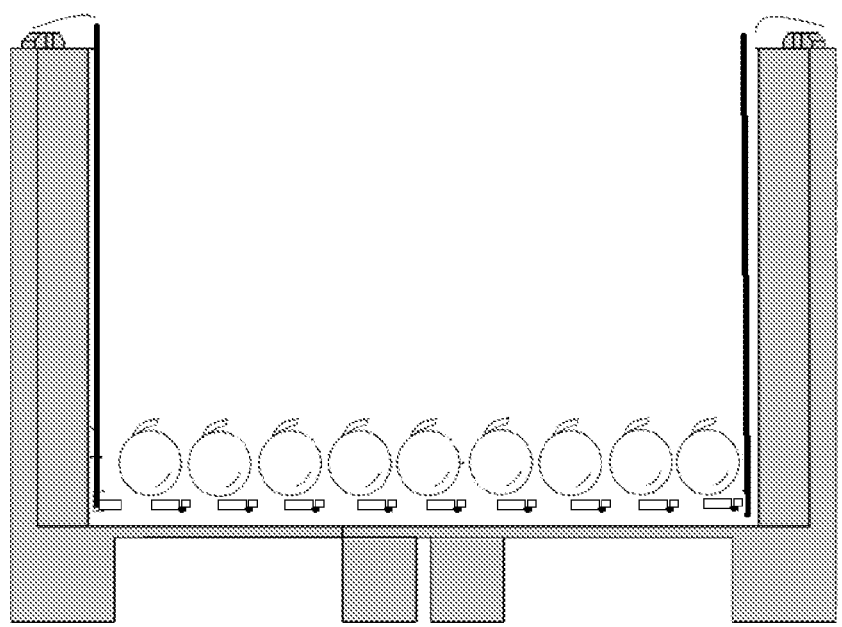
Figure 6C:
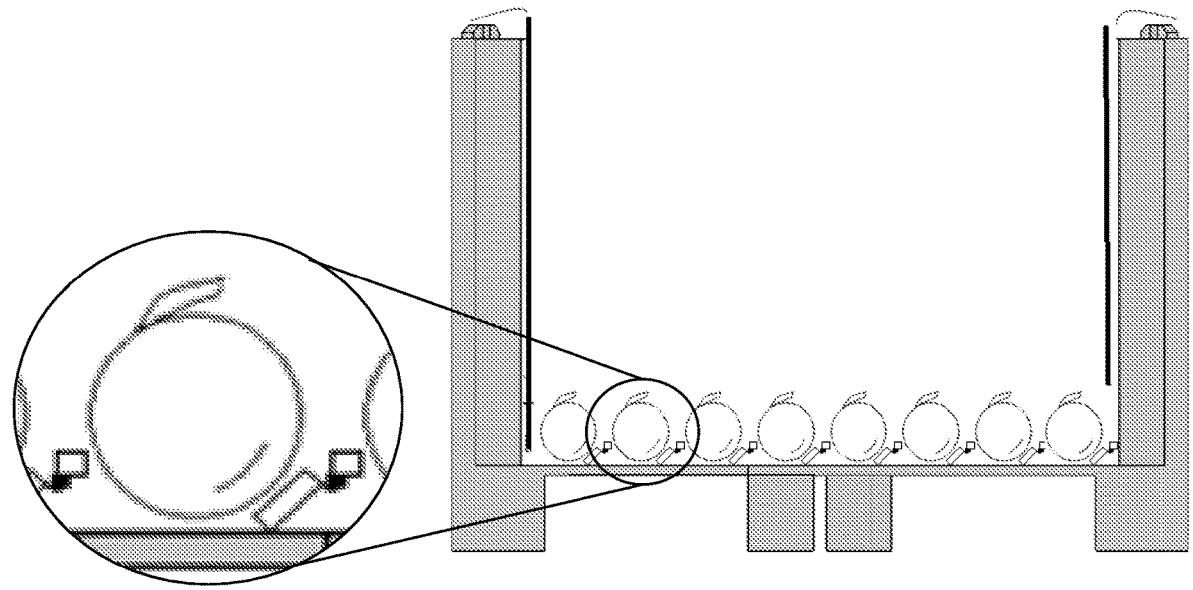
Figure 6D:
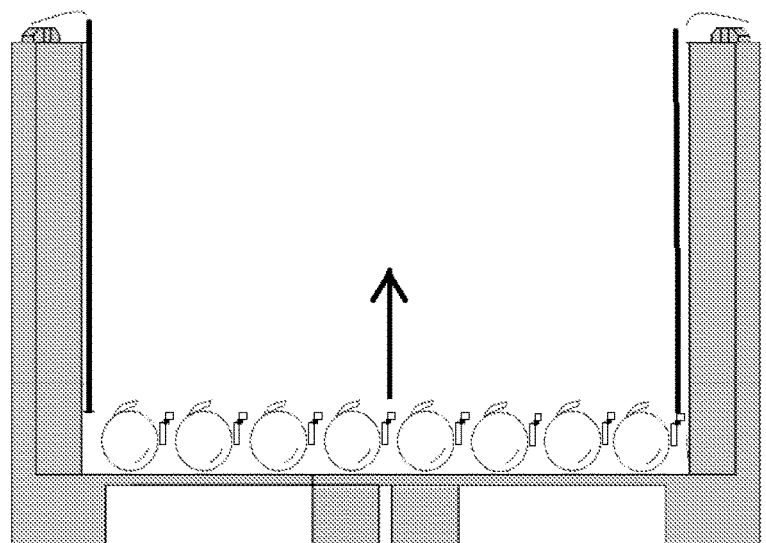
Figure 6E:
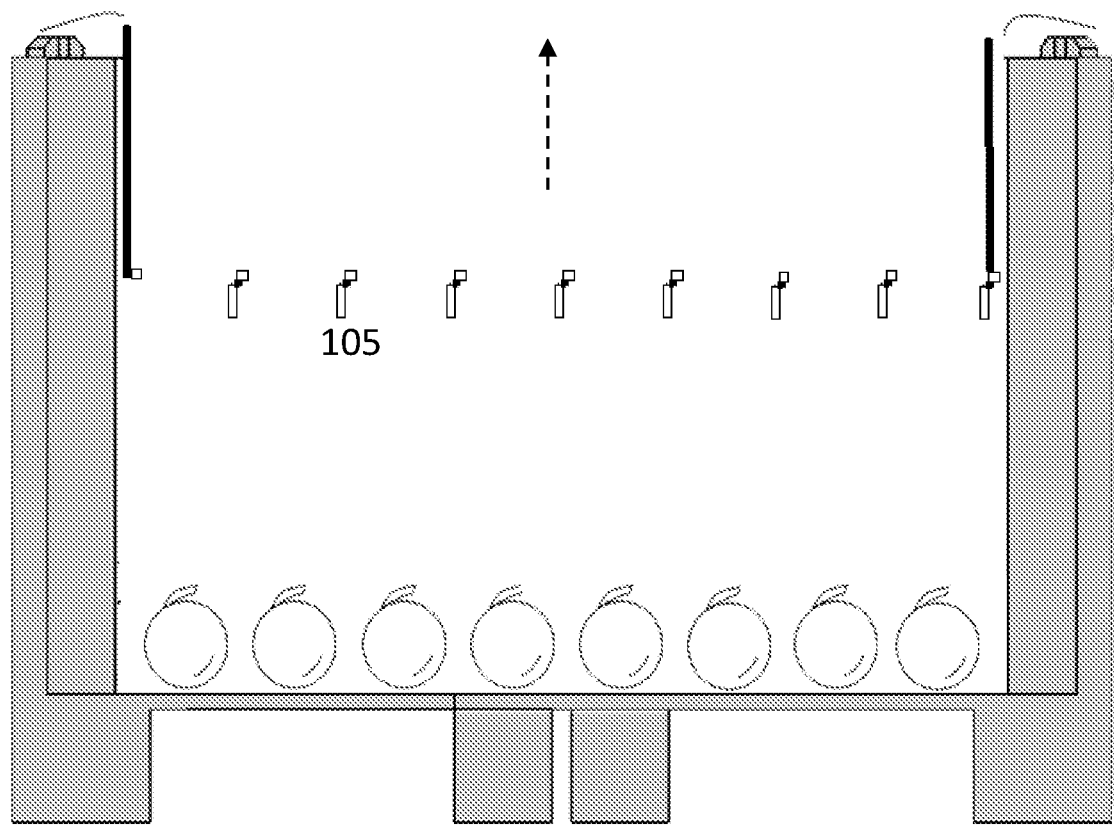

FIGS. 6A-6E illustrate the mechanism of action of another fruit protection system that comprises an elevator floor 105 made of movable fragments that can tilt/bend/fold to generate gaps in between for allowing fruits to pass. As illustrated, at the beginning the elevator floor 105 is position at an upper position enabling safe placement of fruits thereon without the fruits rolling off the floor to the ground and without throwing the fruits into the bottom of the collection bin 101 (FIG. 6A). As illustrated, the fragments comprising the elevator floor 105 do not need to generate a full floor but can create small gaps in between—these gaps are small enough to prevent passage of fruits. Once the elevator floor 105 is full, or reached a predefined weight, it is lowered to the bottom of the collection bin 101 (or to the upper level of fruits within the bin) (FIG. 6B)—this lowering is either according to gravity or electrically by motor(s) controlled by an integrated computing system. When the elevator floor 105 has reached the lowest possible position (either at the bin's bottom or the upper level of fruits within the bin), the fragments tilt/bend/fold—either electrically or by releasing a safety lock (FIG. 6C), thereby generating gaps through which fruits can pass (FIG. 6D) as the elevator floor 105 is lifted up (FIG. 6E). When the elevator floor 105 returns to its upper position, the fragments return to their place creating a floor onto which fruits can be placed. This procedure continues until the collection bin 101 is full.

Figure 7A:
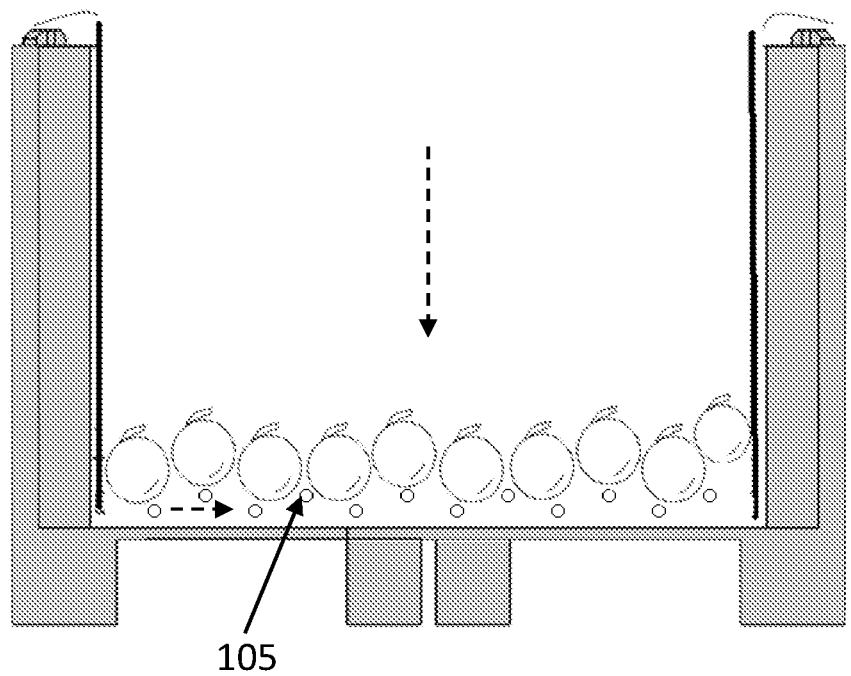
FIGS. 7A-7E illustrate another configuration of an elevator floor/floating floor according to the invention comprising rod-shaped floor segments that once move enable fruits to pass therethrough when the elevator floor reaches the bottom of the collection bin.
Figure 7B:
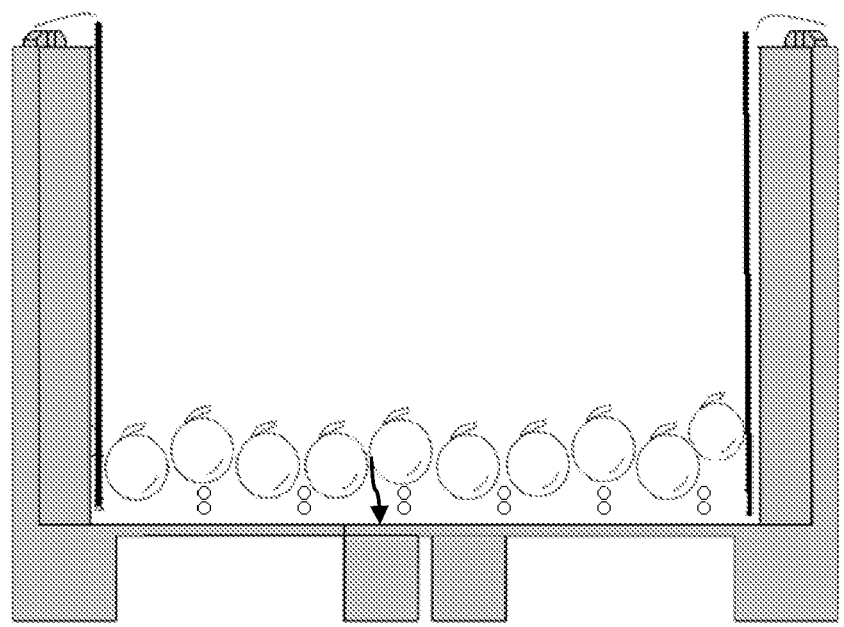
Figure 7C:
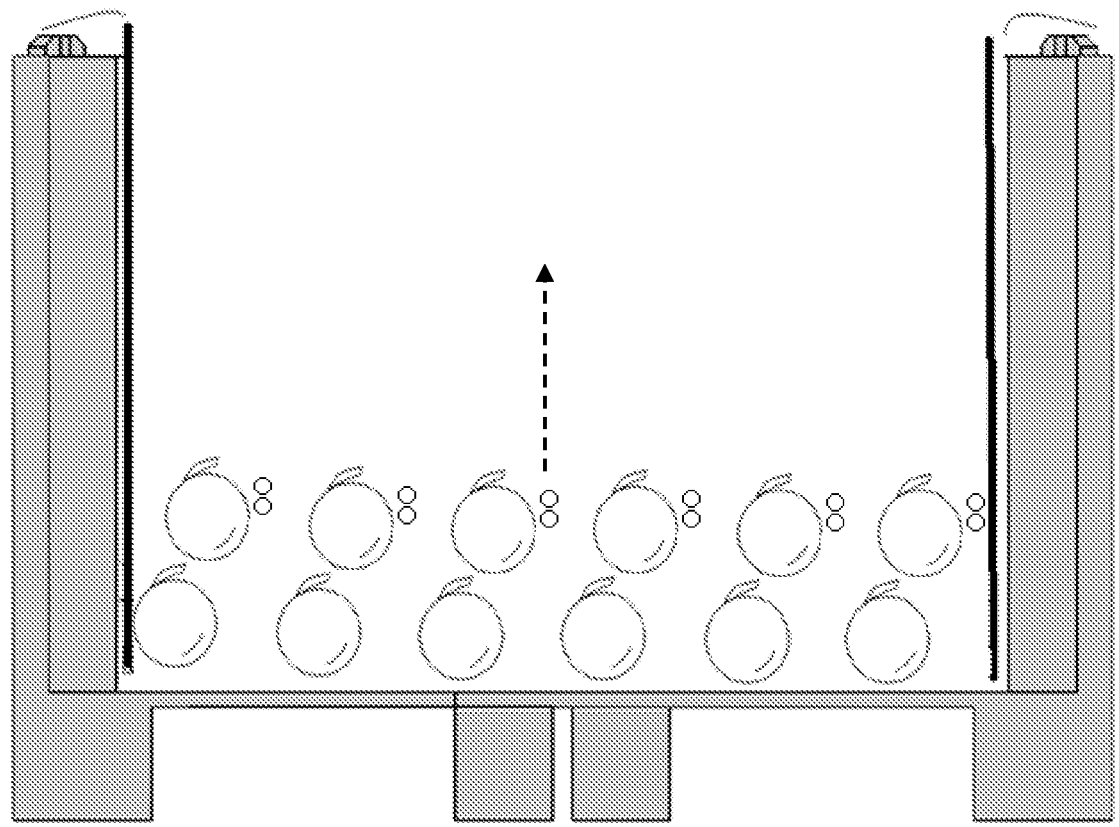
Figure 7D:
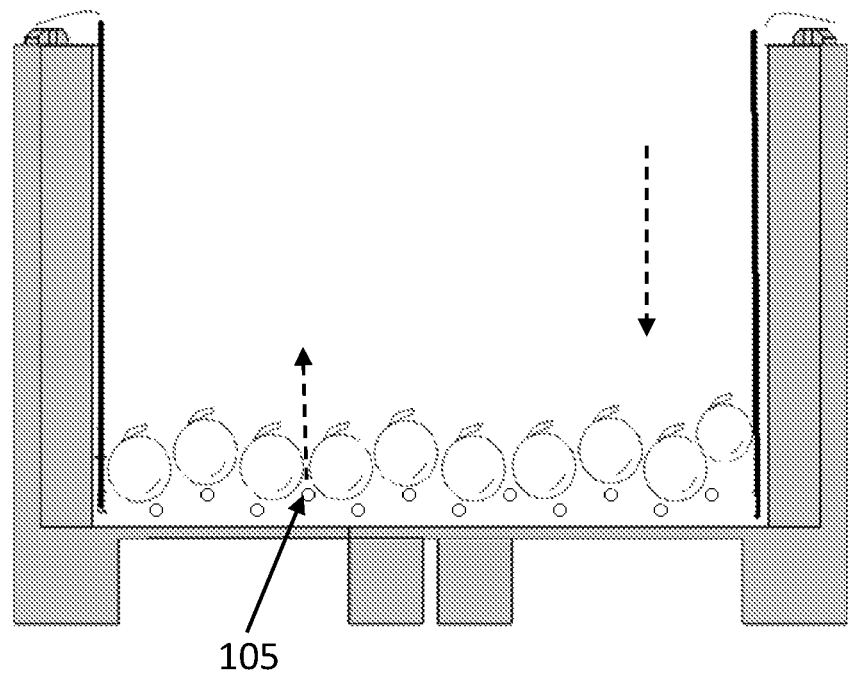
Figure 7E:
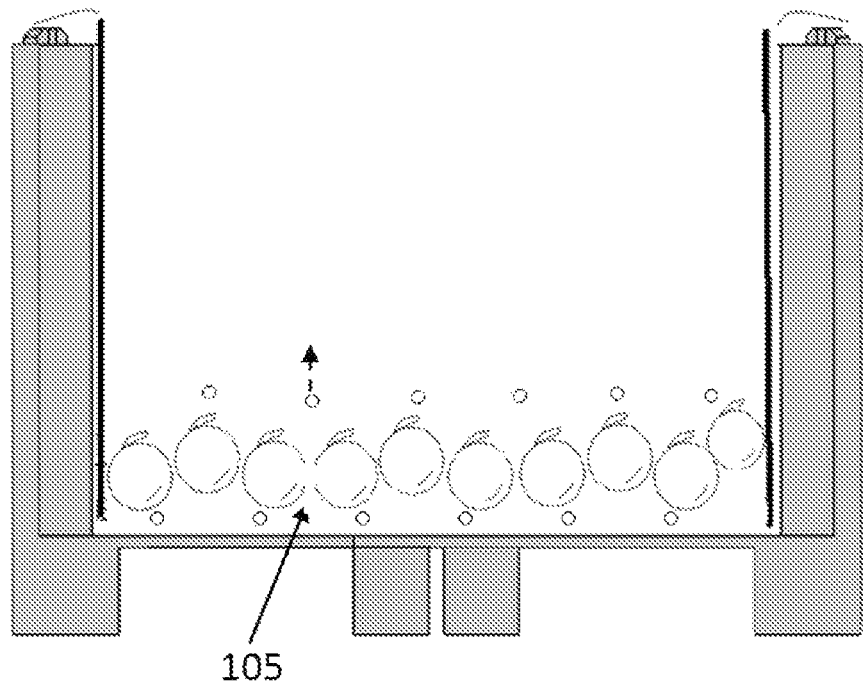

FIGS. 7A-7C illustrate the mechanism of action of yet another fruit protection system that comprises an elevator floor 105 made of movable rods/fragments that are positioned spaced apart from one another while still preventing passage of fruits therethrough. These movable rods/fragments can move towards one another to increase the gaps therebetween to thereby allow fruits to pass. As illustrated, once the elevator floor 105 is full, or reached a predefined weight, it is lowered to the bottom of the collection bin 101 (or to the upper level of fruits within the bin) (FIG. 7A)—this lowering is either according to gravity or electrically by motor(s) controlled by an integrated computing system. When the elevator floor 105 has reached the lowest possible position (either at the bin's bottom or the upper level of fruits within the bin), the movable rods/fragments move towards one another, e.g., in an overlapping manner (FIG. 7B) or up/down relative to one another (FIG. 7E), thereby increasing the gaps between them through which fruits can pass (FIG. 7B) as the elevator floor 105 is lifted up (FIG. 7C). In specific embodiments, when the floating floor reaches the lowest possible point in the collection bin, the movable rods/fragments move apart from one another, e.g. up and/or down relative to one another, thereby increasing the gaps therebetween and allowing fruits to pass therethrough (FIGS. 7D and 7E). This can be done as part of the returning of the elevator floor to its upper position, e.g. by first moving one (e.g. the upper rods) up, and subsequently lifting the other rods up. It should be noted that the movement of the rods is not necessarily in a straight line but can also be in a zig-zag route. When the elevator floor 105 returns to its upper position, the movable rods/fragments return to their original place creating a perforated floor onto which fruits can be placed without falling through. This procedure continues until the collection bin 101 is full.

Figure 8A:
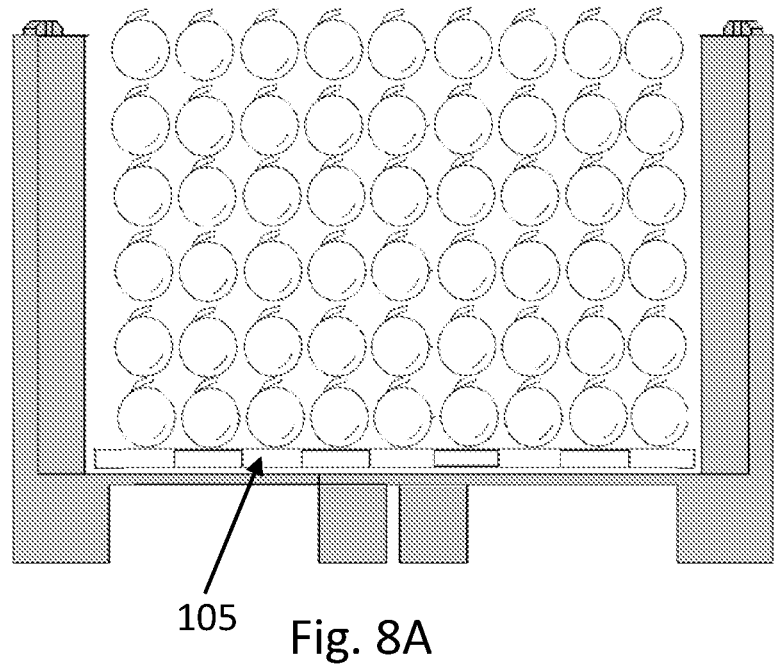
FIGS. 8A-8B illustrate another configuration of an elevator floor/floating floor according to the invention comprising retractable floor segments.
Figure 8B:
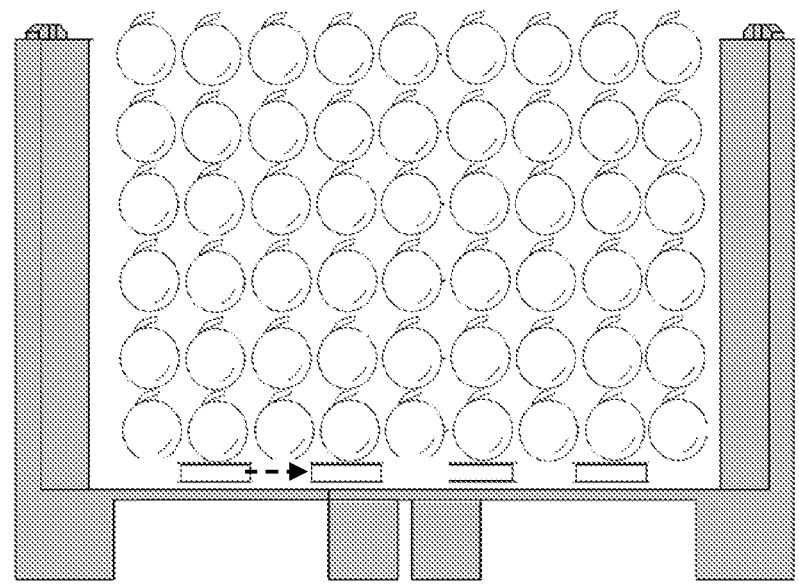

FIGS. 8A-8B illustrate the mechanism of action of a fruit protection system that comprises an elevator floor 105 made of movable/shiftable fragments that can slide towards one another to generate gaps in between for allowing fruits to pass. At the beginning the elevator floor 105 is position at an upper position enabling safe placement of fruits thereon without the fruits rolling off the floor to the ground and without throwing the fruits into the bottom of the collection bin 101. As fruits pile, the elevator floor 105 is slowly lowered until it reaches the bottom of the collection bin 101 (FIG. 8A)—this lowering is either according to gravity or electrically by motor(s) controlled by an integrated computing system. When the elevator floor 105 has reached the bin's bottom, the movable/shiftable fragments move towards one another—either in an overlapping manner or into one another (FIG. 8B), thereby generating gaps through which fruits can pass as the elevator floor 105 is lifted up.

When the elevator floor 105 returns to its upper position, the fruit protection system can be dismantled/removed from the collection bin 101 and optionally assembled onto an empty collection bin 101.

The invention claimed is:

1. A fruit protection system for use with a fruit collection bin for protecting fruits from damage during harvesting, the system comprising:
   a) a fruit movable elevator floor/floating floor designed to fit said fruit collection bin; and
   b) at least one retraction mechanism for lifting said elevator floor/floating floor, wherein:
      said elevator floor/floating floor can descend and ascend; and
      said at least one retraction mechanism is:
         an elastic strap(s) or spring(s) designed to be attached to the walls of the collection bin; or
         an electric motor(s), and
      said fruit protection system is designed to be mounted onto and attached to side walls of said fruit collection bin to enable descending said floor inside said bin.

2. The fruit protection system of claim 1, wherein the location/position/height of the floating floor is determined according to the weight of the fruits placed thereon and the retraction force of said at least one retraction mechanism.

3. The fruit protection system of claim 1, wherein when the fruit collection bin is empty, the floating floor is positioned in its upmost upper position, and when the fruit collection bin is completely full, the floating floor is positioned in its: (i) lowest position; or (ii) upmost upper position, without any fruits placed thereon.

4. The fruit protection system of claim 1, wherein said floating floor is made of a flexible and/or disposable material.

5. The fruit protection system of claim 4, wherein said floating floor is a stretchable leash that starches according to the fruits' weight placed thereon.

6. The fruit protection system of claim 4, wherein said floating floor is a stretchable mesh that stretches according to the fruits' weight placed thereon.

7. The fruit protection system of claim 1, wherein said floating floor is made of movable/shiftable fragments having a closed-orientation in which fruits cannot pass between the fragments; and an open-orientation in which fruits can pass between the fragments.

8. The fruit protection system of claim 7, wherein said movable/shiftable fragments move toward one another along a plane parallel to the bottom of the collection bin (into an essentially overlapping position).

9. The fruit protection system of claim 7, wherein said movable/shiftable fragments rotate on an axis that extends in the lengthwise direction of the fragments.

10. The fruit protection system of claim 7, wherein said movable/shiftable fragments move up and/or down relative to one another thereby generating a distance therebetween.

11. A method for preventing/reducing damage to fruits during harvesting, the method comprising the steps of:
   a. mounting and attaching a fruit protection system according to claim 1 onto side walls of a fruits' collection bin;
   b. placing harvested fruits onto the elevator/floating floor of said fruit protection system; and
   c. gradually lowering said elevator/floating floor to the bottom of the collection bin.

12. The method of claim 11, wherein the position of the floating floor is such that the upper surface of the floating floor or the fruits placed thereon is parallel to the upper edge of the walls of said collection bin so that fruits placed thereon do not fall to the bottom of the bin, wherein the lowering of the floating floor is optionally in accordance with the fruits' weight.

13. The method of claim 11, wherein step (c) comprises:
(i) maintaining the position of the floating floor at top position such that the upper surface thereof is parallel to the upper edge of the walls of said collection bin;
(ii) once a predefined weight/amount of fruit is placed on the floating floor, lowering same to the bottom of the collection bin or to the upper surface of the fruits within the bin;
(iii) releasing the fruits from the floating floor (to reside on the bottom of said collection bin or on previously placed fruits);
(iv) lifting the floating floor back to the top position and receiving new fruits; and
(v) repeating the above steps until the collection bin is filled.

14. The method of claim 13, wherein the releasing of the fruits from the floating floor is carried out by opening gaps between fragments that constitute the floating floor.

15. The method of claim 13, wherein the releasing of the fruits from the floating floor is carried out by twisting fragments that constitutes the floating floor thereby creating gaps between adjacent fragments through which fruits can pass.

16. The method of claim 11, wherein a harvesting robot places the fruit on the floating floor uniformly one by one, each time in a different position/location.

* * * * *